United States Patent [19]

Wernau

[11] 4,119,546

[45] Oct. 10, 1978

[54] PROCESS FOR PRODUCING XANTHOMONAS HYDROPHILIC COLLOID, PRODUCT RESULTING THEREFROM, AND USE THEREOF IN DISPLACEMENT OF OIL FROM PARTIALLY DEPLETED RESERVOIRS

[75] Inventor: William C. Wernau, Groton, Conn.

[73] Assignee: Pfizer Inc., New York, N.Y.

[21] Appl. No.: 793,274

[22] Filed: May 3, 1977

Related U.S. Application Data

[63] Continuation-in-part of Ser. No. 711,843, Aug. 5, 1976, abandoned.

[51] Int. Cl.$^2$ ........................ E21B 43/20; C12B 1/00; C12D 13/04

[52] U.S. Cl. ................................ 252/8.55 D; 166/246; 166/305 R; 195/31 P; 195/96; 195/114

[58] Field of Search ........................ 195/31 P, 114, 96; 252/8.55 D; 166/246, 305 R

[56] References Cited

U.S. PATENT DOCUMENTS

| | | | |
|---|---|---|---|
| 2,867,279 | 1/1959 | Cocks | 252/8.55 D X |
| 3,338,792 | 8/1967 | Patton et al. | 195/31 P |
| 3,391,060 | 7/1968 | McNeely | 195/31 P |
| 3,660,287 | 5/1972 | Quattrini | 166/305 R X |
| 3,853,771 | 12/1974 | Felmann et al. | 252/8.55 D X |
| 3,964,972 | 6/1976 | Patton | 195/31 P |
| 3,966,618 | 6/1976 | Colegrove | 252/8.55 D |

*Primary Examiner*—Richard D. Lovering
*Attorney, Agent, or Firm*—Connolly and Hutz

[57] ABSTRACT

A process is disclosed for preparing a Xanthomonas colloid-containing fermentation broth suitable for the preparation of mobility control solution used in oil recovery which comprises aerobically fermenting a Xanthomonas organism in an aqueous nutrient medium whose ingredients comprise a carbohydrate, a nitrogen source, an assimilable Krebs cycle acid, chelated calcium and trace elements, whereby the whole broth produced provides mobility control solutions of about 100 to 3000 ppm of Xanthomonas colloid which are substantially free of insoluble matter having a particle size greater than about 3 microns.

14 Claims, No Drawings

PROCESS FOR PRODUCING XANTHOMONAS HYDROPHILIC COLLOID, PRODUCT RESULTING THEREFROM, AND USE THEREOF IN DISPLACEMENT OF OIL FROM PARTIALLY DEPLETED RESERVOIRS

CROSS-REFERENCE TO RELATED APPLICATIONS

This application is a continuation-in-part of co-pending application Ser. No. 711,843, filed Aug. 5, 1976, now abandoned.

BACKGROUND OF THE INVENTION

There are extensive published reports relating to the production of hydrophilic colloids by the aerobic propagation of the bacteria of the genus Xanthomonas in aqueous nutrient media. The earliest work in this field was done at The Northern Regional Research Laboratory of The United States Department of Agriculture at Peoria, Illinois and is described in U.S. Pat. No. 3,000,790. Modified fermentation processes are described in U.S. Pat. Nos. 3,020,206; 3,391,060; 3,427,226; 3,433,708; 3,271,267; 3,251,749; 3,281,329; 3,455,786; 3,565,763; 3,594,280; and 3,391,061.

The hydrophilic colloid (xanthan gum) produced by *Xanthomonas campestris* is a polysaccharide which contains mannose, glucose, glucuronic acid, O-acetyl radicals and acetal-linked pyruvic acid in the molar ratio of 2:2:1:1:0.5. The gum and its derivatives have found wide food and industrial applications. Of special interest is the increasing focus on the use of xanthan gum in displacement of oil from partially depleted reservoirs.

Typically, oil is recovered from underground reservoirs via a series of sequential operations. A new well will generally produce a limited amount of oil as a result of release of internal pressure in the well. As this pressure becomes depleted, it is necessary to pump further quantities of oil by mechanical means. These measures recover only about 25% of the total oil stored in the reservoir. A great deal of oil is still trapped within the pores of the formation. Further enhancement of recovery can then be effected by secondary recovery. In one method of recovery a waterflood is carried out by pumping water into a well or series of wells, displacing part of the trapped oil from the porous rock and collecting the displaced oil from surrounding wells. However, waterflooding still leaves about 55-60% of the available oil trapped in the formation. The explanation for this phenomenon is that the water has a very low viscosity compared to the crude oil and tends to follow the path of least resistance, fingering through the oil and leaving large pockets untouched. In addition, surface forces in the formation tend to bind the oil and prevent its displacement.

A number of processes have been developed in recent years to recover further quantities of oil from these reservoirs by the use of mobility control solutions which enhance oil displacement by increasing the viscosity or permeability of the displacing fluid. Of interest are those enhanced recovery processes employing polymer flooding with a polysaccharide or polyacrylamide to increase the viscosity of the displacing fluid. Variations of this process include the use of surfactants and co-surfactants to release the oil from the rock formation. Polyacrylamides have been found to suffer such deficiencies as viscosity loss in brines and severe shear sensitivity. Since, as was well documented in the prior art, xanthan gum is insensitive to salts (does not precipitate or lose viscosity under normal conditions), is shear stable, thermostable and viscosity stable over a wide pH range, xanthan gum is a good displacing agent. Moreover, the gum is poorly adsorbed on the elements of the porous rock formations and it gives viscosities useful in enhanced oil recovery (5 to 90 centipoise units at 1.32 $sec.^{-1}$ shear rate) at low concentrations (100 to 3000 ppm).

The use of solutions of xanthan gum or derivatives of xanthan gum for oil recovery is described in U.S. Pat. Nos. 3,243,000; 3,198,268; 3,532,166; 3,305,016; 3,251,417; 3,391,060; 3,319,715; 3,373,810, 3,434,542 and 3,729,460. It is suggested in U.S. Pat. No. 3,305,016 that aqueous solutions containing the heteropolysaccharide in sufficient quantity to increase the viscosity be employed as the thickening agent in preparing viscous waterflooding solutions. The polysaccharide may be prepared, separated, purified and then added. Alternatively, according to this reference, the entire culture, after adding a bactericide (e.g., formaldehyde) to kill the bacteria, may be added to the flood water.

U.S. Pat. No. 3,000,790 describes the culturing of a Xanthomonas bacterium in a well aerated medium containing commercial glucose, an organic source of nitrogen, dipotassium phosphate and appropriate trace elements. The source of organic nitrogen usually employed is distillers' solubles. The use of this organic nitrogen source contributes a substantial quantity of insolubles to the fermentation broth.

The processes described in U.S. Pat. Nos. 3,000,790, 3,391,060 and the other fermentation processes previously listed yield final fermentation broths that contain substantial amounts of insoluble matter, even when diluted with water, for injection into oil-bearing subterranean formations to impart the necessary and desired mobility control for oil displacement. The particulate matter and in certain cases the Xanthomonas cells in such whole broth would soon plug the oil-bearing formation at the site of injection and thus foul the well and prevent any further oil recovery. Furthermore, the same problem would be encountered with reconstituted xanthan gum precipitated and separated from these fermentation broths. The plugging tendencies of these fermentation broths can be obviated by filtration through diatomaceous earth leaf filters to remove the Xanthomonas cells and particulate and colloidal matter. However, such additional filtering steps are expensive and add significantly to the overall cost factors for enhanced oil recovery.

U.S. Pat. No. 3,853,771 approaches the plugging problem of whole fermentation broths by claiming a process for dissolving or dispersing cellular microorganisms which comprises contacting said materials with an aqueous solution containing at least one surfactant effective for dispersing outer wall layers of microorganism cells, at least one chelating agent for dispersing the inner wall layers of microorganism cells, and at least one alkali metal hydroxide effective for enhancing said dispersing actions.

U.S. Pat. No. 4,010,071 describes a process for clarifying fermentation broths and other aqueous suspensions containing a dissolved xanthan gum and suspended solids resulting from the fermentation by treatment with a minor amount of a protease enzyme. The injectivity of aqueous solutions containing xanthan gum so clarified is improved in oil well flooding operations over solutions not so treated. However, this treatment does not overcome plugging problems due to the presence of insoluble inorganic or non-proteinaceous organic materials present in the fermentation medium or produced during the course of the fermentation.

The object of the process of U.S. Pat. No. 3,391,060 is to recover a polysaccharide product of substantial purity without the use of extensive separation procedures. A high quality, high viscosity, light colored, high purity xanthan gum is recovered from a Xanthomonas fermentation broth. According to this patent, recovery is simplified and elaborate purification procedures are obviated by the replacement of the organic source of nitrogen in the broth with an inorganic source of nitrogen (i.e., ammonium nitrate). However, the fermentation process described therein is not economical because of lengthy reaction times required and low yields of biopolymer obtained.

The method of improving the permeability of mobility control solutions by the addition of certain hydroxy substituted carboxylic acids such as malic, tartaric, citric, gluconic, lactic and salicylic is described in U.S. Pat. No. 2,867,279.

SUMMARY OF THE INVENTION

This invention is concerned with an economical process for preparing a Xanthomonas colloid-containing fermentation broth suitable for preparation of mobility control solutions used in oil recovery which comprises aerobically fermenting a Xanthomonas organism in an aqueous nutrient medium whose ingredients comprise a carbohydrate, a nitrogen source, a Krebs cycle acid, chelated calcium trace ions and iron ions. The whole broth produced provides mobility control solutions of about 100 to 3000 ppm Xanthomonas colloid which are substantially free of insoluble matter having a particle size greater than about 3 microns.

DETAILED DESCRIPTION OF THE INVENTION

The present invention now provides for the first time a practical process for preparing a Xanthomonas fermentation broth which without treatment or clarification provides mobility control solutions for use in oil recovery having a use concentration of about 100 to 3000 ppm Xanthomonas colloid which are substantially free of insoluble matter having a particle size greater than about 3 microns. According to this invention, the whole fermentation broth may be used directly as a mobility control solution such as where the amount of colloid produced during fermentation is within the desired range of use concentration. Alternatively, the broth may be diluted with water or a water solution such as brine to reduce the level of colloid to the desired range. Additives to modify the properties of the mobility control solutions may be employed in addition to the whole or unclarified broths of the present invention.

It has been found that oil in cores from oil fields generally will be effectively recovered by xanthan gum if the polysaccharide solution at use concentration can be made to pass a Millipore filterability test as described later. Typical pore sizes of Millipore filters used for this test are 0.45 to 3.0 microns.

In addition to Millipore filterability, core tests are performed as described by W. B. Gogarty in Mobility Control with Polymer Solutions, Paper (SPE 1566B) presented at the Society of Engineers 41st Annual Fall Meeting held in Dallas, Texas, Oct. 2–5, 1966.

A novel feature of the fermentation broths of the present invention, importantly distinguished from previously reported Xanthomonas fermentation broths and preparations, is the obviated need for expensive and time-consuming filtration or clarification. Important factors that help make this possible are the following:

1. All nutrient ingredients are essentially water soluble or become essentially water soluble during the course of the fermentation or prior to injection.

2. Absolute asepsis is maintained during the course of the fermentation and a bactericide is preferably added at the end of the fermentation.

3. Hard water with high concentrations of calcium ions is preferably not used for the make-up of fermentation media. Low levels of calcium ions (less than about 100 mg/liter, preferably less than about 60 mg/liter) can be sequestered by the addition of a chelating agent such as ethylenediaminetetraacetic acid or preferably citric acid.

4. Amounts of manganese ions may be controlled to avoid seed crystal formation and precipitation of insoluble calcium and phosphate salts (about 0.75 to 60 ppm, preferably 1.5 to 2.4 ppm).

5. Amounts of trace iron are controlled to avoid seed crystal formation and precipitation of insoluble calcium phosphate salts.

Important to the process of the present invention is the incorporation of the following ingredients to promote rapid cell growth and increase xanthan yield while achieving the desired mobility control solutions having substantially no insoluble matter with a particle size above about 3.0 microns.

1. Chelated calcium — about 1 to 200 ppm, preferably about 40 to 60 ppm.

2. Trace iron — about 0.25 to 20 ppm, preferably 0.5 to 8 ppm.

3. Krebs cycle acid — about 0.1 to 10 grams/liter, preferably about 1 gram/liter.

Trace amounts of manganese and ferrous ions are added in the form of such salts as $MnSO_4.H_2O$, $MnCl_2$, $FeSO_4.7H_2O$ and $FeCl_2$.

By Krebs cycle acid is meant an assimilable acid selected from the group consisting of citric acid, oxaloacetic acid, 1-malic acid, fumaric acid, succinic acid and oxalosuccinic acid. Cis-aconitic acid is a Krebs cycle acid that is not useful for the process of this invention. The preferred acid is citric acid because of its added efficiency as a sequestering agent for calcium ions. Citric acid can be incorporated in the fermentation medium at a concentration of about 0.5 to 2 grams/liter, preferably about 1 gram/liter.

In the practice of this invention, a suitable fermentation medium is inoculated with an organism of the genus Xanthomonas. The inoculum medium may be YM Broth (Difco) or a medium containing crude glucose (cerelose), sodium and potassium phosphates, magnesium sulfate and any of a variety of organic sources of nitrogen such as an enzymatic digest of soybean (Soy Peptone Type T, Humko-Sheffield Chemical Co.) or an enzymatic digest of casein (NZ-Amine YT, Humko-Sheffield Chemical Co.). After aerobic propagation for about 30 hours at 28° C., an aliquot is transferred to a fermentor for the second stage inoculum.

A suitable carbohydrate is present in the nutrient medium at a concentration from about 1 to about 5% by weight. Suitable carbohydrates include, for example, glucose, sucrose, maltose, fructose, lactose, processed inverted beet molasses, invert sugar, high quality filtered thinned starch or mixtures of these carbohydrates. The preferred carbohydrates are glucose, maltose, fructose, filtered starch hydrolysates or mixtures thereof.

Inorganic nitrogen is present in the nutrient medium at a concentration of about 0.02 to about 35% by weight, preferably 0.07 to 0.25% by weight. Inorganic nitrate is the preferred nitrogen source; ammonium nitrate at about 1 gram/liter, sodium nitrate at about 2 grams/liter or potassium nitrate at about 2.4 grams/liter may be used. The preferred source of nitrogen in this as well as the production medium is inorganic. However, organic nitrogen sources can also be used although they enhance large Xanthomonas cell formation, provided the overall requirement of substantial freedom from insoluble materials with a particle size above about 3 microns is maintained.

Magnesium in the form of $MgSO_4.7H_2O$ or epsom salts, 0.1 to 1.0 grams/liter, is added along with trace manganese and iron ions. A chelating agent agent such as ethylenediaminetetraacetic acid or preferably citric acid which functions as a growth promoting Krebs cycle acid and sequestering agent for any calcium present is added.

Sufficient mono- and dipotassium phosphates are added to buffer the medium at about pH 5.9 to 8.5, preferably 6.0 to 7.5. After aerobic propagation for about 20–40 hours at 24 to 34° C., preferably 28°–30° C., an aliquot is transferred to a fermentor containing the production medium.

The production medium is similar in composition to that of the second stage inoculum medium with the exception that sodium phosphates are preferably used in place of potassium phosphates because of their lower costs and a small amount of calcium in the form of a salt such as calcium chloride or calcium nitrate or oxide such as lime is added to increase xanthan yield. The amount of calcium added is dependent on the amount of calcium present in the water used for medium make-up, the nitrogen source used and the species and strain of Xanthomonas organism employed. When sodium nitrate or potassium nitrate is used in place of ammonium nitrate, less calcium is required (approximately 27 ppm). Deionized water, distilled water or water containing less than about 20 ppm of calcium and other phosphate precipitable cations may also be used for medium make-up. Calcium ions may be added to a desired concentration. The role of calcium ions in the enhancement of xanthan production is an important one but critical to the process of the present invention is the prevention of the precipitation of excess calcium cations and other cations as insoluble phosphate salts. This is accomplished, when desired, by the addition of a chelating agent such as ethylenediaminetetraacetic acid or other suitable compound known to those skilled in the art at a concentration of about 1 to 20 millimolar, preferably 2 to 8 millimolar.

The pH of the fermentation medium is quite important to suitable growth of the Xanthomonas bacteria. The preferred range is about 6.0 to 7.5. Control of the pH within this range can be obtained by the use of a buffer compound such as disodium acid phosphate. Ethylenediaminetetraacetic acid or other suitable chelating agent is also added in the buffer solution used for pH control to prevent the precipitation of calcium ions introduced in the water used for medium make-up as insoluble calcium salts. The pH is preferably controlled during the fermentation cycle by the addition of sodium or potassium hydroxide solution which has the added advantages of decreasing broth viscosity without affecting xanthan yield and the elimination of the need for chelation of the buffer solution.

In order to obtain a rapid fermentation, it is essential to have the correct amount of oxygen available for the growing bacterial culture. The fermentation medium is aerated to provide sufficient oxygen to produce a sulfite oxidation value within the range of about 1.5 to about 3.5 millimoles of oxygen per liter per minute. A description of sulfite oxidation value is set forth in Industrial Engineering Chemistry 36, 504 (1936). The sulfite oxidation value is a measure of the rate of oxygen uptake in the fermentor under the agitation and aeration conditions employed.

The fermentation is allowed to proceed at a temperature of about 30° C. until the broth has a xanthan concentration of at least about 100 ppm, preferably at least about 1.0% and more preferably at least about 1.4% (30–96 hours). Viscosities of the broth are typically at least about 4,000 centipoise units and preferably at about 7,000 centipoise units.

It is desirable to kill the microbial cells by the addition of a bactericide such as formaldehyde, glutaraldehyde, phenol or substituted phenol such as a cresol or hydroxybenzene or a polyhalogenated phenol such as Corexit (Exxon Corporation), or any other preservative well known in the art. The preferred preservative is formaldehyde at a concentration of from about 200 to 10,000 ppm, preferably about 1000 to 3000 ppm, which can be added to the final fermentation broth before or during storage.

The process of this invention works well for many of the various species of Xanthomonas bacteria. Illustrative species include *Xanthomonas phaseoli, Xanthomonas malvacearum, Xanthomonas carotae, Xanthomonas begoniae, Xanthomonas incanae and Xanthomonas vesicatoria.* The preferred species of *Xanthomonas campestris.*

The Millipore filterability test is an experimental procedure that measures flow rate through a Millipore filter (0.45 to 3.0μ pore size) as a function of volume under a constant pressure of 40 psig. The filter ratio is the ratio of the time to collect the fourth 250 ml of mobility control solution to the time to collect the first 250 ml of mobility control solution. A filter ratio of 1.0 indiates that the solution has no plugging tendencies. An acceptable mobility control solution has a filter ratio of 1 to 3 (0.45 to 3μ Millipore filter), preferably $< 1.7$.

The desired filter ratio and Millipore filter size for testing of a particular mobility control solution are dependent on the permeability of the subterranean stratum of the oil field for which oil displacement is planned.

Mobility control solutions prepared from the whole fermentation broths of the present invention have filter ratios suitable for use in most oil fields. Where subterranean strata are highly impervious, mobility control solutions with low filter ratios must be employed. Under such circumstances, the whole or unclarified broths according to the present invention preferably have substantially no insoluble matter with a particle size in excess of about 0.65μ. This can be accomplished simply by storage of the final fermentation broth in the presence of about 200 to 10,000 ppm formaldehyde for a period of about 3 to 4 days. This aging process shrinks the Xanthomonas cells so that their minor dimension does not exceed 0.65μ in size. Xanthomonas cells are rod-shaped and normally the longer dimension of the cells is greater than 0.65μ whereas the shorter dimension of the cells is about 0.4 to 1.0μ. The storage temperature is not critical and may range from 0° to 135° C., preferably 20° to 45° C. A practical expedient is storage at room temperature for a sufficient period of time so that microscopic examination reveals that the minor dimensions of the Xanthomonas cells are not greater than 0.65μ in size (3–4 days).

The following data show the influence of medium ingredients on the filter ratios of mobility control solutions prepared from aged fermentation broths:

Table I

| | | | Ingredients Level* | | | |
|---|---|---|---|---|---|---|
| Nitrogen Source | $MnSO_4.7H_2O$ (mg/l) | $FeSO_4.7H_2O$ (mg/l) | $CaCl_2.2H_2O$ (g/l) | Citric Acid (g/l) | % Xanthan | Filter Ratio** (0.8 μ pore size) |
| $NaNO_3$ (2 g/l) | 31 | 10 | 0.1 | 1.0 | 1.76 | 1.29 |
| | 15 | 10 | 0.1 | 1.0 | 1.90 | 1.53 |
| | 31 | 5 | 0.1 | 1.0 | 1.86 | 1.54 |
| | 31 | 10 | 0.1 | 0.0 | 1.79 | > 3 |
| | 31 | 10 | 0.2 | 1.0 | 1.79 | > 3 |
| | 31 | 10 | 0.0 | 1.0 | 0.90 | 2.22 |
| $NH_4NO_3$ (1 g/l) | 31 | 10 | 0.2 | 1.0 | 1.94 | 1.47 |
| | 15 | 10 | 0.2 | 1.0 | 1.96 | 1.93 |
| | 31 | 5 | 0.2 | 1.0 | 1.90 | 1.84 |
| | 31 | 10 | 0.2 | 0.0 | 1.57 | > 3 |
| | 31 | 10 | 0.3 | 1.0 | 2.08 | > 3 |
| | 31 | 10 | 0.0 | 1.0 | 1.17 | 2.09 |
| $KNO_3$ (2.4 g/l) | 31 | 10 | 0.1 | 1.0 | 1.72 | 1.54 |
| | 15 | 10 | 0.1 | 1.0 | 1.77 | 1.72 |
| KR(O; (2.4 g/l) | 31 | 5 | 0.1 | 1.0 | 1.80 | 1.33 |
| | 31 | 10 | 0.1 | 0.0 | 1.27 | 1.54 |
| | 31 | 10 | 0.2 | 1.0 | 1.93 | > 3 |
| | 31 | 10 | 0.0 | 1.0 | 0.81 | > 3 |

*All media are made up in distilled water and contain in addition to the listed ingredients D-Glucose 27 g/l; D-Fructose 3 g/l; NaH PO . H O 0.70 g/l; Na HPO 3.34 g/l + 2.445 g/l added at 17 hours.

**All broths diluted to about 750 ppm of xanthan

Table II

| Nitrogen Source | Medium Ingredientss | % Xanthan | Filter Ratio |
|---|---|---|---|
| Fermamine IV | U.S. Pat. No. 3,391,060 | 0.8 | >3 (0.80 μ) |
| Distillers' Solubles | U.S. Pat. No. 3,000,790 | 1.41 | >3 (0.65 μ) |
| NZ Amine YT (2 g/l) | Example II | 0.99 | >3 (0.65 μ) |
| NZ Soy (2 g/l) | Example II | 0.89 | >3 (0.65 μ) |

Alternatively to the aging process, an alkali metal hydroxide such as sodium or potassium hydroxide is added to the final fermentation broth at a concentration of 0.1 to 2.0% w/v, preferably 0.5% w/v, along with an alkali metal salt such as sodium or potassium chloride or sulfate at a concentration of 0 to 5% w/v, preferably 1.0% w/v. The preferred salt is sodium chloride. The broth is heated under an oxygen free atmosphere (e.g., nitrogen) at a temperature of 55°–121° C., preferably 85°–95° C. The heating time is not crucial and may be extended for several hours. A practical time is 1 to 30 minutes, preferably about 10 minutes. The broth is cooled to room temperature and adjusted to pH 3 to 12, preferably 7, with an acid such as hydrochloric acid. This alkaline heat treatment hydrolyzes the bacterial cells without affecting the xanthan content. Deacetylation of the xanthan occurs during this process and the deacetylated product is quite suitable for use in oil recovery.

The suitably aged or alkaline heat-treated fermentation broth is generally diluted with water or brine to a xanthan concentration of about 400 to 1000 ppm for use in enhanced oil recovery. Optionally, a surfactant may be added to enhance the recovery of oil. Representative surfactants include various petroleum sulfonates well known to those versed in the art of oil recovery.

It is understood that there may be conditions and factors that make impractical or expensive the transporation of large volumes of fermentation broth for injection into oil-containing reservoirs. For such purposes a special composition is provided. To the alkaline heat-treated broth previously described is added a water miscible solvent such as methanol, ethanol, acetone, t-butyl alcohol or isopropanol sufficient to precipitate the xanthan gum which is separated by centrifugation or filtration and dried. The preferred water miscible solvent is isopropanol at a concentration of 20–75% w/w, preferably about 38% w/w. Reconstitution with water or brine to a xanthan concentration of 100 to 3000 ppm provides a composition for enhanced oil recovery that is comparable in performance with that of diluted whole fermentation broth. During the process of re-dissolution, it is important to provide sufficient shear to cause adequate dispersion of the polysaccharide and prevention of clump formation.

Test Procedures

Millipore Filterability Test

Prepare 1000 ml of 750 ppm xanthan solution in 500 ppm salt solution (10:1 — $NaCl:CaCl_2$) as follows:

In a Waring type blender equipped with a rheostat, measure sufficient broth (based on xanthan content) to make 0.75 g xanthan solids. Dilute 1 to 6 with salt solution. Shear this mixture as follows:

40% power/2 minutes
60% power/2 minutes
80% power/2 minutes

Dilute in the blender to 750 ppm of xanthan and shear at 40% power for 2 minutes. (Solution also used for viscosity determination).

Use an experimental set-up that allows the flow rate through a Millipore filter disc (47 mm, 0.45–3.0 μ pore size) as a function of volume under a constant pressure of 40 psig. Use a reservoir that will accomodate > 1000 ml.

Change the reservoir with a liter of xanthan solution (750 ppm). Set pressure at 40 psig. Open valve and start recording volume filtrate and time (seconds).

$$\text{Filter Ratio} = \frac{\text{time to collect the 4th 250 ml of solution}}{\text{time to collect the 1st 250 ml of solution}}$$

Viscosity Determination

Measure the viscosity with a Brookfield synchro-lectric viscometer, model LVT, using a UL adaptor. Measure at 25° C. at 6 and 12 RPM. Viscosity is expressed in centipoise units.

Xanthan Determination

Highly purifed xanthan contains about 18.4% glucuronic acid. Glucuronic acid in xanthan compositions is determined in the absence of formaldehyde and without borate at 100° C. by the method of Knutson and Jeanes, Anal. Biochem., 24, 470 (1968); ibid., 482

$$\% \text{ Xanthan} = \frac{\% \text{ Glururonic Acid} \times 100}{18.4}$$

EXAMPLE I

Cells of *Xanthomonas campestris from a YM agar slant are transferred to* 300 ml of YM broth contained in a 2.8-liter Fernbach flask and shaken on a rotary shaker for about 31 hours at 28° C. A 25 ml aliquot is transferred to a 2.8-liter Fernbach flask containing 500 ml of a medium of the following composition:

| Ingredient | | Grams/liter |
|---|---|---|
| Glucose-fructose (Isosweet 100, Corn Products) | autoclave separately | 10.1 |
| Crude glucose (cerelose) | | 25.7 |
| $NH_4NO_3$ | | 1.0 |
| $MgSO_4 . 7H_2O$ | | 0.10 |
| $MnSO_4 . H_2O$ | | 0.03 |
| $FeSO_4 . 7H_2O$ | | 0.01 |
| Anhydrous citric acid | | 1.0 |
| $K_2HPO_4$ | | 4.1 |
| $KH_2PO_4$ | | 0.69 |

The cerelose and Isosweet 100 are dissolved in distilled water and autoclaved. The rest of the ingredients are combined, adjusted to pH 6.4 and autoclaved. The separately autoclaved materials are then combined.

After shaking at 28° C. for about 33 hours. a 200 ml portion is transferred to a 4-liter mechanically agitated fermentor containing 2 liters of medium:

| Ingredient | | Grams/liter |
|---|---|---|
| Cerelose | autoclave separately | 25.7 |
| Isosweet 100 | | 10.1 |
| $NH_4NO_3$ | | 1.0 |
| $MgSo_4 . 7H_2O$ | | 0.10 |
| $MnSO_4 . H_2O$ | | 0.03 |
| $FeSO_4 . 7H_2O$ | | 0.01 |
| Anhydrous citric acid | | 1.0 |
| $CaCl_2 . 2H_2O$ | | 0.20 |
| $Na_2HPO_4$ | | 3.34 |
| $NaH_2PO_4$ | | 0.70 |

The sugars dissolved in 300 ml of water are autoclaved separately. The rest of the ingredients dissolved in 1700 ml of water are autoclaved, and the two solution then combined. Aeration is at a rate to provide 1.5 to 3.5 millimoles of oxygen per liter per minute. The fermentation is conducted at 30° C. for 48 hours during which time the pH of the medium is maintained between 5.9 and 7.5 by the addition of sodium phosphate buffer made up with tap water. Ethylenediaminetetraacetic acid is also added to the sodium phosphate buffer to prevent the precipitation of calcium phosphate salts. At the end of the fermentation, the viscosity of the broth is > 7800 centipoise units (at 6.27 $sec.^{-1}$ shear rate) and the xanthan yield is > 1.5%.

A mobility control solution has a filter ratio of < 1.7 (3.0 μ Millipore filter).

A mobility control solution prepared from whole fermentation broth aged for 4 days has a filter ratio of < 1.7 (0.65 μ Millipore filter).

EXAMPLE II

The method of Example I is repeated employing the following fermentation media:

| Inoculum Medium (1st Stage) Ingredient | | Grams/liter |
|---|---|---|
| Cerelose | | 10.0 |
| $(NH_4)_2HPO_4$ | | 2.0 |
| $KH_2PO_4$ | | 1.0 |
| $MgSO_4 . 7H_2O$ | | 0.5 |
| NZ-Amine YT | pH - 7.0 | 11.0 |

| Inoculum Medium (2nd Stage) Ingredient | | Grams/liter |
|---|---|---|
| D-Glucose | autoclave separately | 27.0 |
| D-Fructose | | 3.0 |
| $NH_4NO_3$ | | 1.0 |
| $MgSO_4 . 7H_2O$ | | 0.10 |
| $MnSO_4 . H_2O$ | | 0.03 |
| $FeSO_4 . 7H_2O$ | | 0.01 |
| Anhydrous citric acid | | 1.0 |
| $K_2HPO_4$ | | 4.1 |
| $KH_2PO_4$ | pH - 6.4 | 0.69 |

| Production Medium Ingredient | | Grams/liter |
|---|---|---|
| D-Glucose | autoclave separately | 27.0 |
| D-Fructose | | 3.0 |
| Anhydrous citric acid | | 1.0 |
| $NH_4NO_3$ | | 1.0 |
| $MgSo_4 . 7H_2O$ | | 0.10 |
| $MnSO_4 . H_2O$ | | 0.03 |
| $FeSO_4 . 7H_2O$ | | 0.01 |
| $CaCl_2 . 2H_2O$ | | 0.20 |
| $Na_2HPO_4$ | | 3.34 |
| $NaH_2PO_4$ | pH - 6.4 | 0.70 |

The fermentation is conducted as in Example I, with comparable results, with the exception that pH adjustment is made with sodium hydroxide solution without the concommitant addition of ethylenediaminetetraacetic acid.

EXAMPLE III

A large scale fermentation is conducted in the following manner:

| Inoculum Medium (1st Stage) Ingredient | | Grams/liter |
|---|---|---|
| Cerelose | | 10.0 |
| $(NH_4)_2HPO_4$ | | 2.0 |
| $KH_2PO_4$ | | 1.0 |
| $MgSO_4 . 7H_2O$ | | 0.5 |
| NZ-Amine YT | pH - 7.0 | 11.0 |

The medium is dispensed in 500 ml portions into two 2.8-liter Fernback flasks. After autoclaving and cooling, the flasks are inoculated with cells of *Xanthomonas campestris.* After shaking for 30 hours at 28° C., the two flasks are combined and used to inoculate a 200 gallon fermentor containing the following ingredients in 100 gallons of medium:

| Inoculum Medium (2nd Stage | |
|---|---|
| Ingredient | Amount (lbs.) |
| Cerelose | 10.0 |
| $(NH_4)_2HPO_4$ | 2.0 |
| $KH_2PO_4$ | 1.0 |
| Epsom salts | 0.5 |
| NZ-Amine YT | 11.0 |
| pH - 7.0 | |

The fermentation medium is stirred with a mechanical agitator and aerated to provide 1.5 to 3.5 millimoles of oxygen per liter minute. Sodium hydroxide solution is added to intervals to maintain the pH at 6.0 to 7.5. Soybean oil is added to control excessive foam. After about 48 hours fermentation, a volume sufficient to provide a 5% v/v inoculum is transferred to a 2000 gallon fermentor containing 800 gallons of medium of the following composition:

| Inoculum Medium (3rd Stage) | | |
|---|---|---|
| Ingredient | | Amount |
| $NH_4NO_3$ (50% solution) | | 1.33 gallons |
| $K_2HPO_4$ | | 27.5 lbs. |
| $KH_2PO_4$ | | 4.75 lbs. |
| Epsom salts | | 306 grams |
| $MnSO_4 . H_2O$ | | 94 grams |
| $FeSO_4 . 7H_2O$ | | 30.5 grams |
| Cerelose | autoclave separately | 175 lbs. |
| Isosweet 100 | autoclave separately | 70 lbs. |
| Anhydrous citric acid | | 6.75 lbs. |
| pH - 7.0 | | |

After fermentation under the previously described conditions for about 31 hours, a sufficient volume to provide a 10% v/v inoculum is transferred to a 2000 gallon fermentor containing 1200 gallons of the following medium:

| Production Medium | | |
|---|---|---|
| Ingredient | | Amount |
| Cerelose | autoclave separately | 297 lbs. |
| Isosweet 100 | autoclave separately | 117 lbs. |
| $NH_4NO_3$ (50% solution) | | 2 gallons |
| Hydrated lime | | 0.73 lbs. |
| Anhydrous citric acid | | 10.0 lbs. |
| $Na_2HPO_4$ | | 33.5 lbs. |
| $NaH_2PO_4$ | | 7.0 lbs. |
| Epsom salts ($MgSO_4 . 7H_2O$) | | 454 grams |
| $MnSO_4 . H_2O$ | | 141 grams |
| $FeSO_4 . 7H_2O$ | | 45.4 grams |
| pH - 7.0 | | |

What is claimed is:

1. A process for preparing a Xanthomonas colloid-containing fermentation broth suitable for the preparation of mobility control solutions used in oil recovery which comprises aerobically fermenting a Xanthomonas organism in an aqueous nutrient medium whose ingredients comprise a carbohydrate, a nitrogen source, about 0.1 to 10 grams per liter of an assimilable Krebs cycle acid, about 1 to 200 ppm chelated calcium, about 0.25 to 20 ppm iron and trace elements until at least about 100 ppm colloid is present in the broth, whereby the whole broth produced provides mobility control solutions of about 100 to 3000 ppm Xanthomonas colloid content which are substantially free of insoluble matter having a particle size greater than about 3 microns.

2. The process of claim 1 wherein a chelating agent is added during the fermentation in an amount of from about 2 to 20 millimolar and said chelating agent is ethylenediaminetetraacetic acid.

3. The process of claim 1 wherein said Krebs cycle acid is citric acid and the concentration of said citric acid in the nutrient medium is about 0.5 to 2 grams per liter.

4. The process of claim 1 wherein a preservative is added to the broth after fermentation in an amount of from about 200 to 10,000 ppm and said preservative is formaldehyde.

5. The process of claim 1 wherein said souce of nitrogen is selected from the group consisting of ammonium nitrate, sodium nitrate and potassium nitrate.

6. The process of claim 1 wherein said aqueous nutrient medium is prepared employing water containing less than 20 ppm of calcium and other phosphate precipitable cations.

7. A process for preparing a Xanthomonas colloid-containing fermentation broth suitable for the preparation of mobility control solutions used in oil recovery which comprises
(a) aerobically fermenting a Xanthomonas organism in an aqueous nutrient medium whose ingredients comprise a carbohydrate, a nitrogen source, about 0.1 to 10 grams per liter of an assimilable Krebs cycle acid, about 1 to 200 ppm chelated calcium, about 0.25 to 20 ppm iron and trace elements until at least 100 ppm colloid is present in the broth, and
(b) storing the broth for 3 to 4 days whereby a hydrophilic colloid-containing fermentation broth substantially free of insoluble matter whose particle size is larger than 0.65 μ is obtained.

8. A hydrophilic colloid-containing fermentation broth obtained by the process of claim 7.

9. In the process for the recovery of crude oil from an oil-bearing subterranean formation wherein a hydrophilic colloid-containing mobility control solution is injected into said formation, the improvement which comprises injecting into said formation a mobility control solution containing a fermentation broth obtained by the process of claim 1.

10. In the process for the recovery of crude oil from an oil-bearing subterranean formation wherein a hydrophilic colloid-containing mobility control solution is injected into said formation, the improvement which comprises injecting into said formation a mobility control solution containing a fermentation broth obtained by the process of claim 7.

11. A process for preparing a hydrophilic colloid-containing fermentation broth suitable for use in the recovery of oil from an oil-bearing subterranean formation by injecting a mobility control solution containing said broth into said formation which comprises
(a) fermenting by aerobic propagation a Xanthomonas organism in an aqueous nutrient medium whose ingredients comprise a carbohydrate, a nitrogen source, about 0.1 to 10 grams per liter of a Krebs cycle acid, about 1 to 200 ppm chelated calcium, about 0.25 to 20 ppm iron and trace elements until at least 100 ppm colloid is present in the broth, and
(b) contacting the broth with from 0.1 to 2.0% w/v concentration of an alkali metal hydroxide and an alkali metal salt at a concentration of from 0 to 5% w/v, heating for 1 to 30 minutes at about 55° to 121° C. under a substantially oxygen free atmosphere and optionally neutralizing.

12. A hydrophilic colloid-containing fermentation broth obtained by the process of claim 11.

13. A process for preparing a hydrophillic colloid suitable for use in the recovery of oil from an oil-bearing subterranean formation by injecting a mobility control solution containing said hydrophilic colloid into said formation which comprises (a) fermenting by aerobic propagation a Xanthomonas organism in an aqueous nutrient medium whose ingredients comprise a carbohydrate, a nitrogen source, about 0.1 to 10 grams per liter of a Krebs cycle acid, about 1 to 200 ppm chelated calcium, about 0.25 to 20 ppm iron and trace elements until at least 100 ppm colloid is present in the broth, and (b) contacting the broth with from 0.1 to 2.0% w/v concentration of an alkali metal hydroxide and an alkali metal salt at a concentration of from 0 to 5% w/v, heating for 1 to 30 minutes at about 55° to 121° C. under a substantially oxygen free atmosphere and optionally neutralizing, and (c) adding sufficient water miscible solvent to cause precipitation of said hydrophilic colloid and separating said precipitated hydrophilic colloid therefrom.

14. A hydrophilic colloid composition obtained by the process of claim 13.

* * * * *

UNITED STATES PATENT AND TRADEMARK OFFICE

CERTIFICATE OF CORRECTION

PATENT NO. : 4,119,546

DATED : October 10, 1978

INVENTOR(S) : William C. Wernau

It is certified that error appears in the above-identified patent and that said Letters Patent are hereby corrected as shown below:

| Column | Line | Correction |
| --- | --- | --- |
| 3 | 33 | Insert comma after "calcium" |
| 5 | 5 | Change "35%" to --0.35%-- |
| 6 | 37 | Change "of" to -- is -- |
| 6 | 45 | Change "indiates" to -- indicates -- |
| Table 1 | | Change "NaNO" to -- $NaNO_3$ -- |
| " | | Change "$NH_4NO$" to -- $NH_4NO_3$ -- |
| " | | Change "KNO" to -- $KNO_3$ -- |
| " | | Delete KR(O (2.4 g/l) |

UNITED STATES PATENT AND TRADEMARK OFFICE

CERTIFICATE OF CORRECTION

PATENT NO. : 4,119,546

DATED : October 10, 1978

INVENTOR(S) : William C. Wernau

It is certified that error appears in the above-identified patent and that said Letters Patent are hereby corrected as shown below:

| Column | Line | Correction |
|---|---|---|
| Table 1 | | Under fine print, change "NaH PO H O" to -- $NaH_2HPO_4$ -- |
| Example 1, Second Medium | | Change "$MgSo_4$" to -- $MgSO_4$ -- |
| Example 2, third Medium | | Change "$MgSo_4$" to -- $MgSO_4$ -- |

Signed and Sealed this

*Twenty-ninth* Day of *May 1979*

[SEAL]

*Attest:*

RUTH C. MASON
*Attesting Officer*

DONALD W. BANNER
*Commissioner of Patents and Trademarks*